United States Patent [19]
Kinnersley et al.

[11] Patent Number: 5,840,656
[45] Date of Patent: Nov. 24, 1998

[54] METHOD FOR INCREASING FERTILIZER EFFICIENCY

[75] Inventors: Alan M. Kinnersley, E. Lansing; Robert D. Coleman, Okemos; Cheng-Yuh Kinnersley, E. Lansing; John L. McIntyre, Alto, all of Mich.

[73] Assignee: Auxein Corporation, Lansing, Mich.

[21] Appl. No.: 744,593

[22] Filed: Nov. 6, 1996

Related U.S. Application Data

[63] Continuation-in-part of Ser. No. 511,498, Aug. 4, 1995, abandoned, which is a continuation of Ser. No. 200,218, Feb. 23, 1994, Pat. No. 5,439,873.

[51] Int. Cl.$^6$ .............................. A01N 3/02; A01N 33/00; C05F 11/00
[52] U.S. Cl. .................... 504/115; 504/116; 504/158; 504/326
[58] Field of Search ................... 504/115, 116, 504/158, 326

[56] References Cited

U.S. PATENT DOCUMENTS

| | | | |
|---|---|---|---|
| 4,491,464 | 1/1985 | Ashmead et al. | 71/11 |
| 4,813,997 | 3/1989 | Kinnersley et al. | 71/66 |
| 4,870,172 | 9/1989 | Okami et al. | 540/460 |
| 4,908,353 | 3/1990 | Yamamoto et al. | 514/19 |
| 4,950,606 | 8/1990 | Stirling et al. | 435/280 |
| 5,143,833 | 9/1992 | Datta | 435/145 |
| 5,593,947 | 1/1997 | Kinnersley et al. | 504/283 |
| 5,597,400 | 1/1997 | Nonomura et al. | 71/28 |

OTHER PUBLICATIONS

"Metabolism, Enzymology & Possible Roles of 4–Aminobutyrate in Higher Plants" (Review article No. 51) V. Satya Narayan and P. M. Nair *Phytochemistry*, 29:367–375, 1990.

"The Production and Efflux of 4–Aminobutyrate in Isolated Mesophyll Cells[1]" Induk Chung, Alan W. Brown & Barry J. Shelp *Plant Physiology;* 99:659–664, 1992.

"Protein and Amino Acid Levels in Leaves of an Interspecies Hybrid & Stock–Components of the Beet in Relation to Growth & Species Specificity" A. F. Marinchik, et al. *Chemical Abstract;* 93:235305n. 1980.

"Polyamine–Induced Prolongation of Storage in Tomato Fruits" David M. Law, et al. *Chemical Abstract;* 116:20002n. 1991.

Solu–Spray Pamphlet by; Leffingwell Chemical Company, 1987.

"Effects of Exogenous Amino acids on in vitro Androgenesis of Datura" R. S. Sangwan *Chemical Abstract;* 99:36050z. 1983.

*Primary Examiner*—S. Mark Clardy
*Attorney, Agent, or Firm*—Woodard, Emhardt, Naughton Moriarty & McNett

[57] ABSTRACT

The specification describes combinations of fertilizer with certain organic compounds to increase fertilizer efficiency, plant productivity, growth, and nutrient accumulation. These beneficial effects are accomplished using combinations of a fertilizer and an amino acid selected from γ-aminobutyric acid, glutamic acid, and a mixture of γ-aminobutyric acid and glutamic acid. A source of proteinaceous amino acids and a carbon skeleton may also be used with the fertilizer and the amino acid. The specification describes compositions and methods employing such combinations to take advantage of their beneficial effects.

19 Claims, No Drawings

METHOD FOR INCREASING FERTILIZER EFFICIENCY

CONTINUING DATA

This application is a continuation-in-part application of application Ser. No. 08/511,498, filed Aug. 4, 1995, now abandoned, which is a continuation of application Ser. No. 08/200,218, filed Feb. 23, 1994, now U.S. Pat. No. 5,439,873.

FIELD OF THE INVENTION

The present invention relates to methods and compositions for effectively reducing fertilizer usage while maintaining or increasing plant productivity levels.

BACKGROUND OF THE INVENTION

In recent years there has been a growing concern with the environmental impact of fertilizer use, particularly nitrogen fertilizers, on water and atmospheric pollution. Limits on fertilizer use have been legislated in several countries, and further restrictions are expected in the future. In spite of the call to reduce fertilizer usage, greater use of fertilizers will be necessary in the future to support food and fiber production for rapid population growth on limited land resources. World population growth is predicted to be 6 billion by the end of the century and 10.5 billion by 2050. See, Byrnes, B. H. "Environmental effects of N fertilizer Use—An Overview", Fertilizer Research 26:209–215 1990.

Because of the predicted world population growth, methods to increase fertilizer efficiency are needed to ensure expanded food production while minimizing the impact of fertilizers on the environment. The economical benefits of reducing fertilizer usage are considerable. It has been estimated that a ⅓ reduction in global fertilizer usage would result in the saving of $10 billion annually. "Global Possible", World Research Institute, R. Repello, Ed., Yale University Press, 1985, p. 248. Therefore, a need exists for an effective method to increase fertilizer efficiency while reducing fertilizer usage and its adverse environmental impacts.

SUMMARY OF THE INVENTION

This invention addresses the need for increased fertilizer efficiency while reducing fertilizer usage. Fertilizer efficiency is improved by use of a combination of a fertilizer and an amino acid selected from γ-aminobutyric acid (GABA), glutamic acid, and a mixture of γ-aminobutyric acid and glutamic acid. In the preferred embodiments discussed in the detailed description below, a source of proteinaceous amino acids and/or a hydrocarbonaceous compound may also be used with the fertilizer and amino acid combination.

A first embodiment of the invention relates to a method for increasing the efficiency of a fertilizer. The method comprises providing a fertilizer and an amino acid selected from γ-aminobutyric acid, glutamic acid, and a mixture of γ-aminobutyric acid and glutamic acid to a plant. The amino acid is used in an amount which effectively increases the efficiency of the fertilizer.

A second embodiment of the invention provides a method for increasing the accumulation of nutrients by a plant. In this method a fertilizer and an amino acid are applied to a plant in a combined amount effective to increase the accumulation of nutrients by the plant. The amino acid is selected from γ-aminobutyric acid, glutamic acid, and a mixture of γ-aminobutyric acid and glutamic acid.

A method for increasing plant growth represents a third embodiment of the invention. This method also employs a fertilizer, and an amino acid selected from γ-aminobutyric acid, glutamic acid, and a mixture of γ-aminobutyric acid and glutamic acid. The fertilizer and the amino acid are applied to a plant in a combined amount effective to stimulate plant growth.

A fourth embodiment of the invention relates to a method for increasing plant productivity using a fertilizer, and an amino acid selected from γ-aminobutyric acid, glutamic acid and a mixture of γ-aminobutyric acid and glutamic acid. The fertilizer and the amino acid are provided to a plant in an amount effective to increase plant productivity.

The invention provides an improved fertilizer composition as a fifth embodiment of the invention. The improved fertilizer composition contains a fertilizer, and an amino acid selected from γ-aminobutyric acid, glutamic acid, and a mixture of γ-aminobutyric acid and glutamic acid. The fertilizer and the amino acid are present in the fertilizer composition in a combined amount effective to increase plant growth. Other embodiments of the invention will be apparent from the following detailed description.

DETAILED DESCRIPTION OF THE INVENTION

The present invention provides combinations of fertilizer with an amino acid selected from γ-aminobutyric acid, glutamic acid and a mixture of γ-aminobutyric acid and glutamic acid. The combination increases fertilizer efficiency as well as increases plant productivity, plant growth and nutrient accumulation. Additionally, the combination permits reduced amounts of fertilizer to be used. Accordingly, the invention relates to compositions and methods which take advantage of these beneficial effects.

The methods and compositions of the invention may be used with commercial, recreational, or decorative plants or crops. The invention is particularly useful for treating commercial crops. For example, such plants or crops include, but are not limited to, monocots, for example duckweed or corn and turf (such as rye grass, Bermuda grass, blue grass, fescue, and the like), as well as dicots, which include for example, crucifers (such as rape seed, radishes, and cabbage), legumes (such as bush beans, snap beans, and soybeans), and solanaceae (such as green peppers, potatoes, and tomatoes).

As is known in the art, fertilizers are materials added to the soil or to a plant (e.g., the foliage of a plant) to provide nutrients necessary for plant growth and productivity. See, Kirk-Othmer, "Concise Encyclopedia of Chemical Technology", John Wiley & Sons, New York, 1985. Fertilizers may be divided into three classes based upon the nutrients supplied: primary-nitrogen (N), phosphorous (usually $P_2O_5$), and potassium (expressed as $K_2O$); secondary-calcium (Ca), magnesium (Mg), and sulfur (S); and minor or micronutrients-iron (Fe), manganese (Mn), copper (Cu), zinc (Zn), boron (B), and molybdenum (Mo). For the purposes of the present invention, a composition is a fertilizer if it at least contains a source of plant nutrients and is applied to a plant or its surrounding soil to supply those nutrients.

Any fertilizer may be used in the practice of the invention, and the fertilizer may be applied to plants at the same time, prior to, or subsequently to providing the plants with the other components of the invention. The fertilizer is not limited by its use with commercial, recreational, or decorative plants or crops. In other words, the present invention may be used in any situation where a fertilizer is applied to nourish a plant. Exemplary fertilizers include, but are not limited to, SOLUSPRAY™ 20-20-20, available from Leffingwell Chemical Co., of Brea, Calif.; SCOTT'S LIQUID LAWN FERTILIZER, NPK composition 27:1:2) available from The Scotts Company, of Marysville, Ohio; Peter's 20-20-20 fertilizer, available from Grace Sierra, Milpitas, Calif. A non-limiting example of a fertilizer which may be used is Peter's 20-20-20 fertilizer which contains:

| | |
|---|---|
| Total Nitrogen (N) | 20% |
| 3.90% Ammoniacal Nitrogen | |
| 6.15% Nitrate Nitrogen | |
| 9.95% Urea Nitrogen | |
| Available Phosphoric Acid ($P_2O_5$) | 20% |
| Soluble Potash ($K_2O$) | 20% |
| Derived from: Ammonium, Phosphate, Potassium Nitrate, Urea. | |

As mentioned above, a combination of fertilizer and one or more amino acid has been found to increase fertilizer efficiency as well as stimulate plant growth, productivity and nutrient accumulation. According to the invention, amino acids which exhibit such beneficial and useful properties include γ-aminobutyric acid (GABA), glutamic acid, and mixtures of γ-aminobutyric acid and glutamic acid. These beneficial properties may be further enhanced by combining a source of proteinaceous amino acids and/or a carbon skeleton with the fertilizer/amino acid combination of the invention.

Proteinaceous amino acids may also serve as a source of γ-aminobutyric acid and/or glutamic acid without departing from this embodiment of the invention. Typical sources of proteinaceous amino acids which may be used in the invention are described in "TRADER'S GUIDE TO FERMENTATION MEDIA FORMULATION" 2d Ed., D. W. Zabriske, et al., Traders Protein, Memphis, Tenn., 1980. Preferred sources of proteinaceous amino acids include, protein hydrolysates, (such as casein hydrolysate), blood fermentation media, blood peptone fermentation media, blood protein fermentation media, cotton seed fermentation media, and corn steep liquor. Protein hydrolysates are particularly preferred sources of proteinaceous amino acids. The protein hydrolysate may be an enzymatic digest or an acid hydrolysis product. Casein hydrolysate is a particularly preferred protein hydrolysate.

A carbon skeleton may also be used in combination with the fertilizer and the amino acid to increase the efficiency of a fertilizer and obtain the other beneficial effects discussed above. The term "carbon skeleton" is used to mean any organic compound having more than one carbon atom therein. The carbon is readily metabolizable by the plant. Suitable carbon skeletons are compounds such as carbohydrates and carboxylic acids. The carbohydrates include, for example, glucose, sucrose, and maltose. The carboxylic acids may be, but are not limited to, malic acid, succinic acid, or citric acid as well as salts, esters, or other derivatives of those acids. Preferred carbon skeletons are glucose, sucrose, and succinic acid.

Various types of succinic acid may be used in the present invention. For example, synthetic succinic acid may be used or succinic acid isolated from natural sources or prepared in a fermentation process may also be used. The preparation of fermentation succinic acid is described in co-pending application Ser. No. 08/472,783 which is incorporated here by reference.

In preferred embodiments, both the source of proteinaceous amino acids and the carbon skeleton may be used in conjunction with the fertilizer and amino acid. As discussed and shown below in the Examples, the combination of the fertilizer, amino acid and/or carbon skeleton yields particularly beneficial effects to a plant.

When two or more compounds are combined to give a desired effect, as in the present invention, one of three results is likely to occur. The compounds may combine to give an antagonistic effect being less effective than the compounds if used separately. The combination may yield an additive effect, no greater than the sum of the compounds if used individually. A third effect, which is less likely than an additive effect, is synergism. Synergism exists when the combined effect is greater than the sum of the compounds if used separately. Advantageously, the combinations of the present invention not only increase fertilizer efficiency, but also exhibit synergistic activity to increase plant productivity and growth. The following table shows particularly preferred combinations of fertilizer with an amino acid source and with combinations of an amino acid source and a carbon skeleton:

| PREFERRED COMBINATIONS WITH FERTILIZER |
|---|
| Fertilizer |
| + GABA |
| + GABA + casein hydrolysate |
| + GABA + glucose |
| + GABA + succinic acid |
| + GABA + sucrose |
| + GABA + glutamic acid |
| + GABA + glucose + glutamic acid |
| + GABA + succinic acid + glutamic acid |
| + GABA + sucrose + glutamic acid |
| + GABA + glutamic acid + casein hydrolysate |
| + GABA + glucose + glutamic acid + casein hydrolysate |
| + GABA + succinic acid + glutamic acid + casein hydrolysate |
| + GABA + sucrose + glutamic acid + casein hydrolysate |
| + glutamic acid |
| + glutamic acid + glucose |
| + glutamic acid + succinic acid |
| + glutamic acid + glucose + succinic acid |
| + glutamic acid + sucrose |
| + glutamic acid + casein hydrolysate |
| + glutamic acid + casein hydrolysate + glucose |
| + glutamic acid + casein hydrolysate + succinic acid |
| + glutamic acid + casein hydrolysate + sucrose |

In the first embodiment of the invention, the amino acid is applied in an amount effective to increase the efficiency of the fertilizer. Combining an amino acid with a fertilizer, according to the invention, enables a lower amount of fertilizer to be used without loss of plant growth or, as discussed above, plant productivity or nutrient accumulation. The beneficial effect on plant growth of a combination of fertilizer and amino acid according to the invention may be readily determined by measuring an increase in plant dry weight.

A method for increasing the efficiency of a fertilizer may also be provided by combining a fertilizer, an amino acid, a source of proteinaceous amino acids and/or a carbon skeleton. In combination with a fertilizer, the amino acid, the source of proteinaceous amino acids and/or the carbon skeleton has been found to substantially increase the fertilizer's efficiency.

In the method for increasing the accumulation of nutrients by a plant, increased nutrient accumulation is obtained by applying to a plant a fertilizer and an amino acid selected from γ-aminobutyric acid, glutamic acid and a mixture of γ-aminobutyric acid and glutamic acid. In this method, the fertilizer and amino acid source are applied in a combined amount effective to increase the accumulation of nutrients by a plant. Using such a combination, nutrient uptake increases above that which would be expected from an arithmetic average of nutrient uptake obtained by the use of a fertilizer or amino acid alone. This method is particularly useful for increasing a plant's tissue content of nutrients such as nitrogen, phosphorous, and potassium.

Increased nutrient accumulation may also be obtained by using a combination of fertilizer, amino acid, a source of proteinaceous amino acids and/or a carbon skeleton. Accordingly, use of a combination of fertilizer, amino acid, source of proteinaceous amino acids and/or the carbon skeleton has been found to effectively increase nutrient uptake by the plant.

The methods of the invention may be employed to increase not only a plant's vegetative growth but also a plant's reproductive growth. This is particularly advantageous with crops and other commercial plants. Thus, other various embodiments of the invention provide methods for increasing plant growth as well as plant productivity.

In the method for stimulating plant growth a combination of fertilizer and amino acid are applied to a plant. According to the invention, the amino acid may be selected from γ-aminobutyric acid, glutamic acid, or a mixture of γ-aminobutyric acid and glutamic acid. The fertilizer and the amino acid are applied to a plant in a combined amount effective, preferably synergistically effective, to stimulate plant growth.

As with the other methods of the invention, the method for stimulating plant growth may also be practiced with combinations of fertilizer, amino acid, source of proteinaceous amino acids and/or a carbon skeleton. In those methods, the combined amount of fertilizer, amino acid, source of proteinaceous amino acids and/or the carbon skeleton applied are effective to substantially stimulate plant growth.

Increased plant productivity may also be obtained by providing a combination of fertilizer, amino acid source and a carbon skeleton to a plant. According to the method, the combined amount of fertilizer, amino acid source and carbon skeleton provided to a plant is sufficient to substantially increase plant productivity.

An improved fertilizer composition of the invention may contain a fertilizer and amino acid selected from γ-aminobutyric acid, glutamic acid, and a mixture of γ-aminobutyric acid and glutamic acid and optionally may also contain a source of proteinaceous amino acids and/or a carbon skeleton. In compositions according to the invention, the combined amount of fertilizer, amino acid, source of proteinaceous amino acids and/or the carbon skeleton is effective to substantially increase plant growth.

The compositions of the invention may be either a solid or liquid form, or provided as an additional formulation such as a component of Leffingwell's SOLUSPRAY™ 20-20-20 fertilizer (a solid) or Scott's Liquid Lawn Fertilizer (a liquid). The compositions of the invention may also contain agricultural additives or formulation aids known to those skilled in the art. Such additives or aids may be used to ensure that the fertilizer composition disperses well in a spray tank, sticks to or penetrates plant surfaces (particularly leaf surfaces) as well as to provide other benefits to the plant. For example, surfactants, dispersants, hemectants, humectins, binders, etc. may be used to disperse a composition in a spray tank as well as to allow the composition to adhere and/or penetrate plant surfaces. A pesticide may also be included, to protect the plant from pests or disease.

Preferably, the improved fertilizer composition should be readily dispersable in water or other aqueous systems.

In the practice of the present invention, the compositions containing fertilizer and amino acid alone or together with a proteinaceous amino acid source and/or a carbon skeleton may be provided to the roots, stems and/or foliage of the plant. The various components of the composition may be applied separately or in combination with any other component of the composition. Application of the composition to the roots of a plant may be provided by soil drenching, drip irrigation, or hydroponically. Application to the stems or foliage of a plant may also be provided by spraying the plant with a liquid composition according to the invention or by using a wettable powder to provide slow release of the compound of the composition. Dry formulations may be in the form of granules, dry powders, solution-dispersable powders, pellets and the like. A dry formulation may be spread in the vicinity of the plant or mixed with the soil before or after planting. Water soluble solid compositions may be applied either to the soil, dissolved in the water used for irrigating the plant, or as a foliar application.

Applying a fertilizer and an amino acid with or without a proteinaceous amino acid source and/or a carbon skeleton to plant roots, stems and/or foliage has been found to be effective at preferred concentrations of between about 1 ppm and about 5,000 ppm. The compositions are preferably mixed in a suitable carrier for application to the plants. Suitable carriers include, for example, water or other solvents used in the art. Any source of water such as tap water, well water, irrigation water, or mineralized water may be used. Note that, depending on its location, a particular water source may contain some of the same nutrients as in the fertilizer but generally at much reduced levels. Solutions, such as those prepared according to the present invention are, in general, relatively nonhazardous to the environment.

In order to facilitate a further understanding of the invention, the following examples illustrate certain more specific details of the invention. The examples are not intended to limit the invention. The following abbreviations are used in the examples: Fert=fertilizer, GABA=γ-aminobutyric acid, GLUT=glutamic acid, GLUC=glucose, CAS=casein hydrolysate, GGC=a combination of GABA, glutamic acid and casein hydrolysate, FSA=succinic acid derived from fermentation processes, and SSA=synthetic succinic acid. Elemental analyses reported in the examples were performed by Galbraith Laboratories, Knoxville, Tenn. Unless otherwise stated, the fertilizer combinations used as treatments in the examples were prepared by mixing in tap water.

EXAMPLES 1 AND 2

Duckweed (*Lemna minor L.*) was grown hydroponically following the general procedure in U.S. Pat. No. 5,238,841 (which is incorporated here by reference) except that the nutrient media was replaced with a nutrient composition (40 ml of media per culture with 5–10 cultures per treatment). The nutrient composition contained different levels of fertilizer (Leffingwell's SOLUSPRAY™ 20-20-20 fertilizer) and GABA at 5 mM (Example 1), or GABA at 10 mM+CAS at 1000 ppm or GLUT at 10 mM +CAS at 1000 ppm (Example 2), in tap water. The Duckweed was grown for 3 weeks and plant dry weights were determined to provide a measurement of plant growth. The results for Examples 1 and 2 are given:

EXAMPLE 1

| Treatment | Av. Plant wt. + SD (mg) |
| --- | --- |
| Fert 4.0 g/l | 5.2 ± 1.5 |
| + GABA | 8.4 ± 1.3 |
| Fert 2.0 g/l | 10.0 ± 2.7 |
| + GABA | 21.8 ± 2.2 |
| Fert 1.0 g/l | 13.6 ± 1.8 |
| + GABA | 31.4 ± 5.7 |
| Fert 0.5 g/l | 12.4 ± 2.1 |
| + GABA | 32.4 ± 3.8 |
| Fert 0.25 g/l | 9.4 ± 1.3 |
| + GABA | 35.8 ± 2.5 |

EXAMPLE 2

| Treatment | Av. Plant wt. + SD (mg) |
| --- | --- |
| Fert 4.0 g/l | 7.2 ± 2.2 |
| + GABA/CAS | 41.2 ± 7.0 |
| + GLUT/CAS | 42.5 ± 2.4 |
| Fert 2.0 g/l | 10.5 ± 5.9 |
| + GABA/CAS | 46.0 ± 2.5 |
| + GLUT/CAS | 49.7 ± 3.3 |
| Fert 1.0 g/l | 18.0 ± 2.6 |
| + GABA/CAS | 61.0 ± 9.9 |
| + GLUT/CAS | 70.0 ± 10.4 |
| Fert 0.5 g/l | 15.7 ± 0.9 |
| + GABA/CAS | 74.5 ± 4.6 |
| + GLUT/CAS | 64.0 ± 3.4 |
| Fert 0.25 g/l | 9.5 ± 2.1 |
| + GABA/CAS | 71.5 ± 3.3 |
| + GLUT/CAS | 58.2 ± 5.0 |
| Fert 0.125 g/l | 5.2 ± 0.9 |
| + GABA/CAS | 55.0 ± 5.9 |
| + GLUT/CAS | 51.7 ± 3.4 |

The above results show that when fertilizer levels were reduced below 1.0 g/l (the optimal level for growth) plant dry weight was reduced. Addition of GABA (Example 1) or mixtures of GABA/CAS or mixtures of GLUT/CAS (Example 2) increased plant growth and more than compensated for any decrease in growth due to lower levels of fertilizer. The greatest increases in plant dry weight due to the combination of a fertilizer and GABA, GABA/CAS or GLUT/CAS according to the invention were found at the lowest levels of fertilizer. Plant dry weight increased more than 10-fold in medium containing 10 mM GABA, 1000 ppm CAS, and 0.125 g/l fertilizer over dry weight with 0.125 gl fertilizer alone.

Since the dry weight of plants grown in 0.125 g/l fertilizer +GABA/CAS and GLUT/CAS was higher than that of plants grown with 1.0 g/l fertilizer alone, the results in Table 2 show that formulations of the invention increased fertilizer efficiency at least 8 fold. Elemental analysis of the GABA/CAS or GLUT/CAS nutrient compositions in tap water showed no significant increase in mineral concentration over that of tap water alone. This showed that the GABA/CAS and GLUT/CAS mixtures themselves were not a significant source of plant nutrients.

EXAMPLE 3

To determine the effect fertilizer compositions, according to the invention, have on nutrient uptake, Example 1 was repeated using a medium containing 1 g/l fertilizer (Leffingwell's SOLUSPRAY™ 20-20-20 fertilizer) and GABA at either 1 mM or 10 mM. Elemental analysis of harvested duckweed tissue showed higher levels of accumulated minerals (percentage of mineral per plant dry weight) in plants grown with fertilizer+GABA than in plants grown in media containing fertilizer alone. The results, shown in Table 3, demonstrate that a combination of fertilizer and amino acid, such as GABA, increased nutrient accumulation by plants.

TABLE 3

| | Fert control | Fert + GABA 1 mM g, (% increase) | Fert + GABA 10 mM mM g, (% increase) |
| --- | --- | --- | --- |
| Plant Dry weight | 1.02 g | 1.25 (125%) | 2.38 (238%) |
| Mineral Composition % Dry Weight | | | |
| K % | 2.03 | 2.26 (111%) | 4.20 (207%) |
| N % | 4.94 | 5.02 (102%) | 6.14 (124%) |
| P % | 1.07 | 1.11 (104%) | 1.48 (138%) |
| Ca % | 0.25 | 0.27 (108%) | 0.51 (244%) |
| Mg % | 0.072 | 0.072 (100%) | 0.126 (175%) |

EXAMPLE 4

Bermuda sod was purchased from Oaks Nursery, Knoxville, Tenn., and grown in 4¼" diameter black plastic pots containing Fafard #2 potting soil. Two weeks after transfer to pots, turf was cut and each pot given 50 ml treatment solution. SCOTTS LIQUID LAWN FERTILIZER (Fert) with an N.P.K. of 26:1:2 (0.344 g Fert/pot=2 lbs N/1000 sq. ft.) provided treatments with N dressings equivalent to ½, 1, 2, and 4 lbs N/1000 sq. ft. For a combination of the invention, one treatment contained Fertilizer at ½ lb N and GABA at 5 mM. Each treatment consisted of ten replicate pots. The turf was harvested one week after treatment, and the average dry weight of turf was determined. The results below, in Table 4, show the average dry weight from ten pots for each treatment.

TABLE 4

| Treatment | Av. Dry Wt. (mg) ± SD |
| --- | --- |
| control-no treatment | 335 ± 87 |
| Fert ½ lb N | 448 ± 107 |
| Fert 2 lb N | 640 ± 229 |
| Fert ½ lb N + GABA 5 mM | 644 ± 214 |

Statistical analysis of the data using the student's t-test showed that weight of turf treated with fertilizer at the equivalent of ½ lb Nitrogen per 1000 sq. feet+GABA was significantly greater (t≧0.95) than turf treated with ½ lb N fertilizer alone. The weight of grass from the treatment receiving GABA was not significantly different from that of the treatment receiving four times as much fertilizer. The foregoing example demonstrates that addition of GABA increased fertilizer efficiency four fold.

EXAMPLE 5

Bermuda sod was purchased from Oakes nursery (Knoxville, Tenn.) and grown in 4¼" diameter pots containing Fafard #2 potting soil. There were 10 pots in each replicate. Once the turf had been established (1 week after potting), the turf was given an aqueous nutrient solution, 50 ml/pot, containing various amounts of SCOTT'S LIQUID LAWN FERTILIZER (Fert) alone or combined with 1000 ppm each of GABA, GLUT, and CAS (GGC) as shown in the Table 5, below. Table 5 shows the amounts of nutrients in each solution and a tap water control. The turf was harvested one week later and the dry weights determined. The turf was also analyzed to determine its mineral content by elemental analysis. The results are shown in Table 6.

TABLE 5

MINERAL CONTENT OF TREATMENT SOLUTIONS

| Nutrient Solution | Percentage Nitrogen | Phosphorous Conc. (ppm) | Potassium Conc. (ppm) | Calcium Conc. (ppm) |
|---|---|---|---|---|
| Tap water | <0.07 | 0.02 | 2 | 39 |
| Fert ½ lb | <0.08 | 9.01 | 33 | 37 |
| Fert 1 lb | <0.09 | 18.0 | 63 | 37 |
| Fert 4 lb | <0.33 | 70.4 | 237 | 36 |
| Fert ½ lb GGC (1000 ppm each) | <0.07 | 8.9 | 33 | 37 |

TABLE 6

DRY WEIGHT AND MINERAL CONTENT OF TREATED TURF

| Nutrient Solution | Av. Dry Wt. | Percent Nitrogen | Percent Phosphorous | Percent Potassium | Percent Calcium |
|---|---|---|---|---|---|
| Tap Water | 438 ± 108 | 3.3 | 0.36 | 1.8 | 0.49 |
| Fert ½ lb | 479 ± 138 | 3.6 | 0.41 | 2.1 | 0.50 |
| Fert 1 lb | 650 ± 254 | 3.8 | 0.40 | 2.1 | 0.56 |
| Fert 4 lb | 720 ± 287 | 4.1 | 0.43 | 2.3 | 0.57 |
| Fert ½ lb + GGC (1000 ppm each) | 718 ± 174 | 4.3 | 0.46 | 2.3 | 0.63 |

As shown in Table 5, treating Bermuda grass with ½ lb fertilizer and GGC yielded essentially the same dry weight as grass treated with 4 lb of fertilizer. Thus, the GGC increased fertilizer efficiency 8-fold. Statistical analysis of the results showed that the weight of the turf treated with the GGC-containing nutrient solution was significantly heavier (at a 99% confidence level) than turf given the ½ lb of fertilizer alone.

The above results also showed that the nutrient accumulation in the harvested turf was directly related to the nutrient content of the nutrient solution, with one exception, the turf with the GGC-containing nutrient solution. As shown in Table 6, the amount of nitrogen in the harvested turf control samples was directly related to the amount of nitrogen in the tap water and fertilizer-only nutrient solutions. In contrast, while the GGC-containing nutrient solution has a nitrogen content no higher than the nutrient solution containing ½ lb Fertilizer alone, the turf treated with the GGC-containing nutrient solution had a nitrogen content higher than that of turf treated with 4 lb of Fertilizer, i.e., 8 times the amount of fertilizer.

Similar results were achieved with respect to the other nutrients. The percentage of phosphorous, potassium, and calcium in the turf treated with the GGC-containing nutrient solution was as high or higher than the nutrient content of the turf treated with 4 lb of Fertilizer. Yet, the nutrient content of the GGC-containing nutrient solution itself was no different from that of the nutrient solution containing ½ lb Fertilizer alone.

These results demonstrated that combinations of fertilizer and a source of amino acids according to the invention effectively increased nutrient accumulation in a plant. These results also demonstrated that such combinations permit the use of a reduced amount of fertilizer without reducing plant growth or nutrient accumulation by the plants. Thus, the compositions of the invention increase fertilizer efficiency.

EXAMPLE 6

Rye grass seed (Helton Hardware, Knoxville, Tenn.) was germinated in 1 gallon pots filled with Fafard #2 potting soil. Two weeks after grass had germinated, grass was cut and 100 ml of treatment solutions given per pot. Each treatment had five pots and treatments were Scotts Liquid Lawn Fertilizer (Fert, ½ lb N/1000 sq. ft.) with and without 5 mM GABA. Grass in each treatment was harvested ten days later and grass dry weights and mineral composition determined. The samples of grass from each treatment were analyzed to determine the mineral content. Results are shown in Table 7 below:

TABLE 7

| | Fertilizer Control | Fertilizer + GABA 5 mM | % Change |
|---|---|---|---|
| Av. Dry Wt (g) | 1.062 | 1.480 | 139 |
| Av. Dry Wt* | 0.738 | 1.015 | 137 |
| Element | | | |
| N % | 2.55 | 3.44 | 135 |
| P % | 0.60 | 1.14 | 190 |
| K % | 3.30 | 7.89 | 239 |
| Ca % | 0.53 | 0.87 | 164 |
| Mg % | 0.42 | 0.82 | 195 |
| Na % | 0.11 | 0.18 | 164 |
| S % | 0.63 | 0.83 | 131 |
| Zn ppm | 53 | 124 | 234 |
| Fe ppm | 116 | 170 | 147 |
| Mn ppm | 425 | 534 | 126 |
| B ppm | 7 | 11 | 157 |
| Cu ppm | 7 | 13 | 186 |

Results above demonstrated that treating plants with fertilizer solutions containing 5 mM GABA increased plant growth, as shown in harvested dry weight data, and also increased the mineral content of the grass, with potassium (+239%) showing the greatest increase. Average dry weight (Av. Dry Wt.*) is the dry weight of grass taken two harvests after treatments had been given, showing that the beneficial effects of GABA treatments were sustained in subsequent harvests, even without further treatments.

EXAMPLE 7

Seeds of rye grass were obtained from Helton Hardware, Knoxville, Tenn. The Rye grass seed was germinated and was grown in 4¼" diameter black plastic pots containing Fafard #2 potting soil. There were 8 sets of 10 replicate pots for each treatment. Each set of 10 pots received a different treatment, as shown in Table 8. After the grass was established, it was cut and each set of pots was given 50 ml of nutrient solution containing the amount of SCOTT'S LIQUID LAWN FERTILIZER (Fert) with or without 500 ppm GABA, 500 ppm glutamic acid, and 500 ppm casein hydrolysate, (GGC at 500 ppm each), as shown in Table 8. The grass was harvested two weeks later and the grass dry weights determined. The results are shown in Table 8.

TABLE 8

| Treatment | Av. Grass Dry Wt. (mg/pot) | % Change From Fertilizer |
|---|---|---|
| Fert 1 lb | 414 | |
| Fert 1 lb + GGC | 429 | 104 |
| Fert 2 lb | 473 | |
| Fert 2 lb + GGC | 529 | 123 |
| Fert 4 lb | 516 | |
| Fert 4 lb + GGC | 550 | 107 |
| Fert 8 lb | 397 | |
| Fert 8 lb + GGC | 465 | 117 |

These results demonstrated that fertilizer combined with the amino acids GABA and GLUT and with a source of proteinaceous amino acids, such as CAS, stimulated plant growth. Plant growth stimulation was observed at levels of fertilizer that were optimal for grass growth (4 lb), super optimal (8 lb), as well as growth limiting (1 lb).

EXAMPLE 8

Duckweed was grown as described in Examples 1 and 2 except that the nutrient media consisted of water, fertilizer, or fertilizer and 5 g/l glucose with and without GLUT or CAS. The fertilizer used was Leffingwell SOLUSPRAY™ 20-20-20 fertilizer at 1 g/l, (Fert). The results in Table 9 show the effect on the plants' average dry weight of the different treatments.

TABLE 9

SYNERGISTIC GROWTH RESPONSE OF FERTILIZER, GABA AND GLUTAMIC ACID

| Treatment (at 500 ppm) | Av. Plant Dry Wt. +/− SD (mgs) | Exp.* | A/E** |
|---|---|---|---|
| Water cont. | 0 | | |
| + GABA | 4 +/− 1 | | |
| + GLUT | 12 +/− 2 | | |
| + CAS | 30 +/− 5 | | |
| + CAS + GABA | 30 +/− 3 | | |
| + CAS + GLUT | 27 +/− 2 | | |
| + CAS + GLUT + GABA | 31 +/− 5 | | |
| Fert cont. | 114 +/− 1 | | |
| + GABA | 152 +/− 12 | 118 | 1.29 |
| + GLUT | 212 +/− 6 | 126 | 1.69 |
| + CAS | 149 +/− 5 | 144 | 1.00 |
| + CAS + GABA | 184 +/− 11 | 144 | 1.28 |
| + CAS + GLUT | 232 +/− 6 | 141 | 1.64 |
| + CAS + GLUT + GABA | 245 +/− 6 | 145 | 1.70 |

*Treatments were added to culture media containing glucose (5 g/L) in water or SOLUSPRAY 20-20-20 fertilizer (1 g/L).
**The expected dry weight is the sum of the individual components of the mixture.
***A/E values greater than 1 show synergy. A (The actual increase in dry weight)/E (the expected increase in dry weight) provides a measure of the unexpected growth response due to synergy.

The increase in growth seen when GABA, GLUT and CAS were provided to a plant in an aqueous carrier fluid showed the nutritional value of these components. CAS (casein hydrolysate), a mixture of amino acids, was found to be much more effective at promoting plant growth than the single amino acids GABA and glutamic acid. There was no significant difference between the effects on growth of CAS by itself and CAS+GLUT or CAS+GLUT+GABA.

When the same treatment was performed with compositions according to the invention, such as compositions containing fertilizer and glutamic acid, quite different results were obtained. Fertilizer+GLUT was significantly more effective at promoting plant growth than Fertilizer+CAS. Moreover combinations of CAS+GLUT and CAS+GLUT+GABA had an additive effect on growth promoting activity which was unexpected from the activity of these components in an aqueous carrier fluid. This unexpected effect showed a powerful synergy between fertilizer and GABA, GLUT and CAS in promoting duckweed growth.

Results in Table 9 enable the degree of synergy to be quantified. For example water containing GABA+GLUT+CAS produced 31 mgs plant dry weight whereas fertilizer alone produced 114 mgs. The combination of fertilizer+GABA+GLUT+CAS produced 245 mgs dry weight or 100 mgs more than the expected 145 mgs which is the sum of the individual components. In other words, plant growth was 1.7 times greater than expected because of a synergistic effect.

EXAMPLE 9

Example 8 was repeated to show the effect of different concentrations of an amino acid (GLUT) and a carbon skeleton (GLUC) on the synergistic response. The results are shown in Table 10.

TABLE 10

| Treatment | Av. plant Dry wt. + SD (mg) | exp. | A/E |
|---|---|---|---|
| Fert 1 g/l | 15 ± 3 | | |
| + GLUC 30 mM (540 ppm) | 64 ± 3 | | |
| + GLUC 60 mM | 75 ± 4 | | |
| + GLUC 100 mM | 101 ± 4 | | |
| + GLUT 2 mM (294 ppm) | 16 ± 3 | | |
| + GLUT 4 mM | 19 ± 3 | | |
| + GLUT 8 mM | 24 ± 3 | | |
| + GLUT 16 mM | 37 ± 8 | | |
| + GABA 8 mM | 23 ± 3 | * | |
| + GLUC 30 mM + GLUT 2 mM | 89 ± 6 | 65 | 1.37 |
| + GLUC 30 mM + GLUT 4 mM | 125 ± 12 | 68 | 1.84 |
| + GLUC 30 mM + GLUT 8 mM | 145 ± 11 | 73 | 1.99 |
| + GLUC 60 mM + GLUT 4 mM | 158 ± 20 | 79 | 2.00 |
| + GLUC 60 mM + GLUT 8 mM | 190 ± 69 | 84 | 2.26 |
| + GLUC 100 mM + GLUT 16 mM | 297 ± 12 | 118 | 2.51 |
| + GLUC 60 mM + GABA 8 mM | 142 ± 25 | 83 | 1.71 |

*The expected growth increase = the sum of the individual components-15 since each of the individual components has a fertilizer component contributing to growth.

The above results showed a synergistic response between a fertilizer, an amino acid and a carbon skeleton according to the invention, and this response was exhibited over a wide range of concentrations. In these results, greater synergy occurred at higher concentrations as shown by the high A/E ratio.

EXAMPLE 10

Example 8 was again repeated to demonstrate a synergistic effect between another combination of a fertilizer, an amino acid, and carbon skeletons, specifically fertilizer and GABA with succinic acid or glucose. The succinic acid (SSA) used in this example was purchased from Sigma Chemical Co., St. Louis, Mo. The amount of each component in the nutrient medium and the results are shown in Table 11.

TABLE 11*

| Treatment | Av Plant Dry Wt. ± SD (mg) | Exp. | A/E |
|---|---|---|---|
| Fert 1 g/l | 15 ± 2 | | |
| + SSA 750 ppm | 22 ± 3 | | |

TABLE 11*-continued

| Treatment | Av Plant Dry Wt. ± SD (mg) | Exp. | A/E |
| --- | --- | --- | --- |
| + GABA 250 ppm | 26 ± 6 | | |
| + SSA 750 ppm | 40 ± 8 | 33 | 1.21 |
| + GABA 250 ppm | | | |
| Fert 1 g/l | 8 ± 2 | | |
| + GLUC 750 ppm | 23 ± 1 | | |
| + GABA 250 ppm | 16 ± 1 | | |
| + GLUC 750 ppm | 38 ± 1 | 31 | 1.23 |
| + GABA 250 ppm | | | |

*See notes to Table 9.

EXAMPLE 11

Bush beans ("Peanut Beans") (Mayo Seeds, Knoxville, Tenn.) were planted in rows following grower instructions in the field. The field had been given a dressing of 545 lb/acre with an 18-18-18 fertilizer. Field plots were tilled, cultivated, watered and maintained with insecticide and herbicide on an "as needed" basis by the Horticulture Teaching and Research Center of Michigan State University. Treatments were replicated six times and each replicate consisted of three plants. The treatments included a control (water alone), fertilizer at 1 lb, 5 lb, or 10 lb/100 gallons levels, and fertilizer at 1 lb/100 gallons with 300 ppm, 1000 ppm, or 3000 ppm GGC. For the GGC, each treatment contained equal amounts of GABA, GLUT, and CAS each to make up the total GGC amount. Plants were given three foliar applications of treatments at weekly intervals with the first application given at the first visible sign of bean formation (approximately five weeks after seed planting). Rates of application were 100 gal/acre. Plants were harvested one week after the third application. Table 12 shows the results.

TABLE 12

| Treatment[a] | No. of Beans | Bean Wt. (kg) |
| --- | --- | --- |
| Control | 831 | 2.993 |
| Fert 1 lb | 1485 | 4.815 |
| Fert 5 lb | 1749 | 5.271 |
| Fert 10 lb | 1440 | 4.884 |
| Fert 1 lb + GGC 300 ppm | 1680 | 5.829 |
| Fert 1 lb + GGC 1000 ppm | 1344 | 4.191 |
| Fert 1 lb + GGC 3000 ppm | 1317 | 4.456 |

[a]= Experiment performed over about 10.5 weeks.

The results in Table 12 showed that for bush beans treated with foliar application of fertilizer and GGC at 300 ppm, bean productivity was increased 21% over plants given same level of fertilizer and 11% over plants given 5-times more fertilizer.

The experiment was repeated using GGC at 150 ppm (50 ppm each of GABA, GLUT, and CAS) and GGC at 300 ppm (100 ppm each of GABA, GLUT, and CAS). The results are shown in Table 13.

TABLE 13[a]

| Treatment | Avg. No. Beans ± SD | Avg. Bean Wt. (g) ± SD | Avg. Plant Dry Wt. (g) ± SD |
| --- | --- | --- | --- |
| Fert 1 lb | 10.5 ± 1.7 | 33.3 ± 8.6 | 24.4 ± 7.5 |
| Fert 5 lb | 11.2 ± 2.3 | 38.4 ± 8.9 | 27.1 ± 5.0 |
| Fert 1 lb + GGC (150 ppm) | 12.8 ± 2.0 | 40.8 ± 7.6 | 31.8 ± 8.8 |
| Fert 1 lb + GGC (300 ppm) | 12.1 ± 2.2 | 41.7 ± 9.4 | 31.9 ± 7.9 |

[a]= Experiment performed over approximately 9 weeks.

Fertilizer and GGC (150 ppm) increased bean productivity by 22.5% over same level of fertilizer and 8% over 5 times more fertilizer. This confirms the yield increases found with 300 ppm GGC in previous the example.

Elemental analysis of the bean plants was used to determine the effect on nutrient uptake (percentage of mineral per plant dry weight). The results are shown in Table 14.

TABLE 14

| | 1 lb Fert | 5 lb Fert | 1 lb Fert + GGC (150 ppm) | 1 lb Fert + GGC (300 ppm |
| --- | --- | --- | --- | --- |
| Avg. Plant Dry Wt. | 24.4 ± 7.5 | 27.1 ± 5.0 | 31.8 ± 8.8 | 31.9 ± 7.9 |
| Mineral Composition % Dry Wt. | | | | |
| N % | 2.78 | 2.85 | 2.76 | 2.68 |
| P % | 0.273 | 0.260 | 0.244 | 0.205 |
| K % | 1.46 | 1.45 | 1.57 | 1.56 |
| Ca % | 3.98 | 3.57 | 3.56 | 3.16 |
| Mg % | 0.947 | 0.909 | 0.873 | 0.722 |

These results demonstrated that the compositions of the invention increased accumulation of potassium in plants. Table 14 showed that GGC-treated plants had 30% greater biomass, as shown by plant dry weight, than plants treated with fertilizer alone. Elemental analysis of the plant tissue showed a higher level of potassium for the GGC-treated plants than plants given 5 times more potassium. The results indicated that GGC in combination with fertilizer increased plant potassium levels, which is associated with increased plant growth and productivity.

EXAMPLE 12

In the greenhouse, Cherry Belle radishes (Mayo Seeds, Knoxville, Tenn.) were planted in 4.25" diameter round black plastic pots containing Fafard #2 potting soil (Conrad Fafard, Aganawa, Mass.). After germination, seedlings were thinned to 3/pot. Each treatment consisted of 30 replicate pots. Foliar applications (spray to drip) of the treatments shown in Table 15 were given 10 days and 17 days after planting. The fertilizer used was Leffingwell's SOLUS-PRAY™ fertilizer. Plants were harvested after four weeks and fresh weights of the plants and radishes were determined. The results are shown in Table 15.

TABLE 15

| Treatment | Avg. Fresh Wt. (g ± SD) | |
| --- | --- | --- |
| | Foliage | Radish |
| Water Control | 4.1 ± 3.1 | 2.9 ± 2.3 |
| Fert 1 lb | 5.7 ± 2.8 | 3.7 ± 2.2 |
| Fert 1 lb + GLUT + CAS (1000 ppm each) | 7.7 ± 4.6 | 5.7 ± 4.4 |
| Fert 1 lb + SSA 750 ppm + GABA 250 ppm | 7.6 ± 4.7 | 5.2 ± 3.7 |

The results given in Table 15 showed that combinations according to the invention stimulated increased root and foliage growth in radishes as compared to the control sample and to a plant treated with fertilizer alone.

EXAMPLE 13

Rocdor Snap Bean seeds were germinated in twenty-five 5" diameter pots containing baccto soil. The bean plants were thinned to 3 plants per pot. The pots were then split into two plots for low and high humidity conditions. A greenhouse having a temperature of 82° F. and 65% humidity with cloudy skies provided the low humidity conditions. High humidity conditions were generated by placing plastic bags over the plants after treatment. After 10 days the plants were treated with nutrient solutions containing 20,000 mg/L Leffingwell's SOLUSPRAY™ fertilizer (Fert) with or without a mixture containing 250 mg/L, 500 mg/L, or 1000 mg/L each of GABA, GLUT, and CAS (GGC). A control was run without fertilizer or GGC. The plants were harvested 12 days later. The fresh and dry weights of the harvested plants were determined. The results, shown in Table 16, include plants grown under low and high humidity: i.e., all plants were harvested and their weights determined.

TABLE 16

| Treatment | Plant Fresh Wt., g | Plant Dry wt., g |
| --- | --- | --- |
| Control | 10.44 | 2040 |
| Fert | 10.86 | 2140 |
| Fert + GGC (250 ppm) | 10.38 | 1970 |
| Fert + GGC (500 ppm) | 11.64* | 2220** |
| Fert + GGC (1000 ppm) | 10.80 | 2120 |

*Statistically different from other treatments, p < 0.01.
**Statistically different from other treatments, p < 0.05.

The results given in Table 16 showed that when the amount of GGC used with the fertilizer was increased to 500 ppm, significant increase in both plant fresh weight and plant dry weight was experienced. Moreover, the average plant dry weight for low and high humidity was 2,190 and 2,030 respectively, with a statistical probability of p<0.01.

EXAMPLE 14

Seeds of a self-compatible fast-growing variety of rapeseed were obtained from the Crucifer Genetics Cooperative at the University of Wisconsin. Seeds were grown in one gallon pots containing Baccto professional planting mix (Michigan Peat Co., Houston, Tex.). Three weeks following seeding, the germinated plants were treated with a foliar spray (spray to drip) or each pot was given the spray formulation as a drench, 40 ml/pot. The plants were treated with nutrient solutions containing 1.2 g/L Leffingwell's SOLUSPRAY™ fertilizer (Fert) with or without 100 ppm each of GABA, GLUT, and CAS (GGC), 1000 pm SA; or 100 ppm each GGC and 1000 ppm succinic acid (SA). The plants were then treated one week and two weeks later and then harvested after eight weeks. There were seven plant replicates/treatment. The results given in Tables 17 and 18 below provide the total number of seed pods, the total weight of the seed pods, the total weight of five replicate plants harvested from each treatment, and the total vegetative dry weight of the plants. Table 17 shows the results of the foliar spray application and Table 18 contains results from drench application of the compositions.

TABLE 17

| Treatment | Seed Pods (% change) | Pod Dry Wt. g (% change) | Plant Dry Wt. g (% change) | Veg. Dry Wt. g (% change) |
| --- | --- | --- | --- | --- |
| Fert | 328 (100%) | 3.37 (100%) | 11.51 (100%) | 7.54 (100%) |
| Fert + GGC (300 ppm) | 349 (106%) | 3.06 (77%) | 12.94 (112%) | 9.88 (131%) |
| Fert + SA (1000 ppm) | 217 (66%) | 3.58 (90%) | 11.23 (98%) | 7.65 (101%) |
| Fert + GGC (300 ppm) + SA (1000 ppm) | 378 (115%) | 4.33 (109%) | 13.92 (121%) | 9.59 (127%) |

TABLE 18

| Treatment | Seed Pods (% change) | Pod Dry Wt. g (% change) | Plant Dry Wt. g (% change) | Veg. Dry Wt. g (% change) |
|---|---|---|---|---|
| Fert | 235 (100%) | 3.37 (100%) | 13.07 (100%) | 9.70 (100%) |
| Fert + GGC (300 ppm) | 240 (102%) | 4.72 (140%) | 10.54 (81%) | 5.82 (60%) |
| Fert + SA (1000 ppm) | 213 (91%) | 3.56 (106%) | 10.74 (82%) | 7.18 (74%) |
| Fert + GGC (300 ppm) + SA (1000 ppm) | 290 (123%) | 5.84 (173%) | 14.64 (112%) | 8.80 (91%) |

The above results with rapeseed confirmed the results shown in prior Examples with duckweed. The results showed that combinations of fertilizer+GGC+SA according to the invention further increased the synergism between the fertilizer and GGC. When used as a soil drench and as a foliar application, the fertilizer+GGC+SA formulation gave the greatest increase in reproductive growth (dry weight of seed pods).

EXAMPLE 15

Potatoes, Snowden variety, were planted at the Michigan State University Montcalm Potato Research Farm. The nitrogen rate and time of application were variables, evaluated for selected test formulations. The plants were first treated, by spraying, when they were 8 to 10 inches in height. Just before flowering, the second treatment was applied by spraying. All plots were top-dressed with sixty pounds of nitrogen per acre 3 weeks after planting. The high nitrogen plots received an additional 100 pounds per acre 5 weeks after planting. The potatoes were harvested 4½ months after planting. The marketable yield of the potato tubers was graded in USDA number 1, small or "B" size and culls. The values in Table 19 show the marketable tuber yield. The amounts of SSA, GABA, GLUT and CAS are measured by the percentage of total weight per treatment.

TABLE 19

| Treatment | Marketable Tuber Yield (lb/plot) | | |
|---|---|---|---|
| Nitrogen Content | high | low | high |
| Carrier | water | water | Fert |
| FSA, prep B | 24.5 | 18.9 | NT |
| FSA, prep C | 23.9 | 18.1 | NT |
| SSA (85%) + GABA (15%) | 24.3 | 20.9 | 24.8 |
| SSA (85%) + GLUT (15%) | 24.9 | 18.4 | 24.5 |
| SSA (80%) + GLUT (15%) + CAS (5%) | 24.9 | 19.8 | 23.9 |
| Control (Carrier Only) | 22.8 | 16.5 | 23.8 |

Fert = Leffingwell's SOLUSPRAY ™ 5 lb/acre
NT = not tested

The results given in the Table showed that combinations according to the invention elevated marketable tuber yield by increasing the weight of the treated potatoes, which is an example of how the invention elevates crop yield.

EXAMPLE 16

Corn (Pioneer 3751) was seeded at the Michigan State University Agronomy Research Farm. Carrier, nitrogen rate and time of application were variables, evaluated for the test formulations. The plants were divided into two groups. One-half of the plants were sprayed after four weeks of growth, when the corn was in the V6 stage (6 leaves). These same plants received a second application three weeks later when the plants were in the V13 stage. The second half of the plants were not sprayed after the first four weeks, while in the V6 stage. Instead, these plants were sprayed with the appropriate material after seven weeks, the V13 stage, at the same time the first half of the plants received their second treatment. The application of foliar sprays at both the V6 and V13 stages was 40 gallons/acre.

The corn was harvested after 5 months of growth. Counts of ears and stalks per plot and grain yield were determined. The values given in Table 20 show the number of ears per stalk.

TABLE 20

| Treatment | Ears per Stalk | |
|---|---|---|
| Carrier | water | Fert |
| FSA, prep B | 1.31 | NT |
| FSA, prep C | 1.32 | NT |
| SSA (85%) + GABA (15%) | 1.44 | 1.22 |
| SSA (85%) + GLUT (15%) | 1.36 | 1.28 |
| SSA (80%) + GLUT (15%) + CAS (5%) | 1.24 | 1.37 |
| Control (Carrier Only) | 1.21 | 1.21 |

Fert = Leffingwell's SOLUSPRAY ™ 5 lb/acre
NT = not tested

The results provided in Table 20 showed that combinations according to the inventions stimulated corn productivity, as measured by counting the number of ears per stalk of corn, as compared to the control sample. This is another example of increased crop yield, resulting from treatments prepared in accordance with the invention.

EXAMPLE 17

Fieldsport and Charmant varieties of cabbage were grown at the Milton S. Hershey Farms in Hershey, Pa. Pre-plant urea was administered at 150 lb/acre. 1 lb/acre of boron was administered at the same time. A side dress of urea at 200 lb/acre was later provided.

The applications consisted of 3,000 ppm of GGC (1,000 ppm each of GABA, glutamic acid and casein hydrolysate) combined with Leffingwell's SOLUSPRAY™. The LLS (Carrier) concentration was 20,000 ppm. Goldschmidt "Breakthrough" was used as the surfactant at 9 drops/3 liters. All applications were at 96.2 gallons/acre. Four replicates were run for each treatment group and for each variety.

The GCC combined with the fertilizer increased the marketable weights of the two cabbage varieties by 6 percent over the application of the fertilizer alone. The lowest statistical difference between the fertilizer and the fertilizer+GCC was p <0.05.

Although the specification discloses particular embodiments and features of the invention, it is to be understood that the information provided herein is only for purpose of illustrating known embodiments which the invention may take within the scope of the appended claims, and that other embodiments may exist or may be developed in the future within the scope and spirit of the claims all of which are intended to be covered thereby consistent with the law.

The claimed invention is:

1. An improved fertilizer composition comprising:
    a fertilizer and an amino acid component selected from gamma-aminobutyric acid and a mixture of gamma-aminobutyric acid and glutamic acid, whereby the fertilizer and the amino acid are combined in an amount effective to increase plant growth.

2. A composition of claim 1, further comprising a source of proteinaceous amino acids, whereby the fertilizer, the amino acid and source of proteinaceous amino acids are present in a combined amount effective to increase plant growth.

3. A composition of claim 2, further comprising a plant metabolizable organic compound, whereby the fertilizer, the amino acid, source of proteinaceous amino acids, and the plant metabolizable organic compound are effective to increase plant growth.

4. A composition of claim 3, wherein the source of proteinaceous amino acids is casein hydrolysate and the plant metabolizable organic compound is selected from the group consisting of glucose, sucrose and succinic acid.

5. A composition of claim 1, further comprising a plant metabolizable organic compound, whereby the fertilizer, the amino acid and the plant metabolizable organic compound are present in a combined amount effective to increase plant growth.

6. A composition useful for the treatment of plants to improve plant growth which comprises a combination of gamma-aminobutyric acid, glutamic acid and casein hydrolysate in amounts effective to improve plant growth.

7. A composition useful for the treatment of plants to improve plant growth which comprises a combination of gamma-aminobutyric acid and glutamic acid in amounts effective to improve plant growth.

8. A composition useful for the treatment of plants to improve plant growth which consists essentially of a combination of glutamic acid and casein hydrolysate in amounts effective to improve plant growth.

9. A method for treating a plant which comprises:
    treating the plant with a fertilizer and an amino acid component selected from gamma-aminobutyric acid and a mixture of gamma-aminobutyric acid and glutamic acid, the amount of gamma-aminobutyric acid ranging from about 50 to about 1000 ppm and the amount of a mixture of gamma-aminobutyric acid and glutamic acid ranging from about 50 to about 2000 ppm.

10. The method of claim 9, wherein said treating further comprises treating the plant with a source of proteinaceous amino acids in an amount of from about 50 to about 1000 ppm.

11. The method of claim 10, wherein said treating further comprises treating the plant with a plant metabolizable organic compound in an amount of from about 50 to about 5000 ppm.

12. The method of claim 11, wherein the source of proteinaceous amino acids is casein hydrolysate and the plant metabolizable organic compound is selected from the group consisting of glucose, sucrose and succinic acid.

13. The method of claim 9, wherein said treating further comprises treating the plant with a plant metabolizable organic compound in an amount of from about 50 to about 5000 ppm.

14. A method for treating a plant which comprises:
    treating the plant with a composition comprising gamma-aminobutyric acid, glutamic acid and casein hydrolysate.

15. The method of claim 14 in which the gamma-aminobutyric acid, glutamic acid and casein hydrolysate are present in amounts effective to increase plant growth.

16. A method for treating a plant which comprises:
    treating the plant with a composition comprising gamma-aminobutyric acid and glutamic acid.

17. A method for treating a plant which comprises:
    treating the plant with a composition consisting essentially of a fertilizer and glutamic acid, the amount of glutamic acid ranging from about 50 to about 1500 ppm.

18. A method for treating a plant which comprises:
    treating the plant with a composition consisting essentially of glutamic acid and casein hydrolysate.

19. The method of claim 18 in which the glutamic acid and casein hydrolysate are present in amounts effective to increase plant growth.

* * * * *

UNITED STATES PATENT AND TRADEMARK OFFICE
CERTIFICATE OF CORRECTION

PATENT NO. : 5,840,656
DATED : November 24, 1998
INVENTOR(S) : Alan M. Kinnersley et al.

It is certified that error appears in the above-identified patent and that said Letters Patent is hereby corrected as shown below:

In column 7, line 50, please change "gl" to --g/l--.

In column 17, line 37, please change "4%" to --4½--.

Signed and Sealed this

Tenth Day of August, 1999

Attest:

Q. TODD DICKINSON

Attesting Officer

Acting Commissioner of Patents and Trademarks